US010869976B2

(12) United States Patent
Hoysan

(10) Patent No.: US 10,869,976 B2
(45) Date of Patent: Dec. 22, 2020

(54) VENTILATOR MOUNT SYSTEM

(71) Applicant: KONINKLIJKE PHILIPS N.V., Eindhoven (NL)

(72) Inventor: David Hoysan, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 123 days.

(21) Appl. No.: 16/022,755

(22) Filed: Jun. 29, 2018

(65) Prior Publication Data

US 2019/0001089 A1 Jan. 3, 2019

Related U.S. Application Data

(60) Provisional application No. 62/527,071, filed on Jun. 30, 2017.

(51) Int. Cl.
| | | |
|---|---|---|
| A61M 16/00 | (2006.01) |
| A61G 5/00 | (2006.01) |
| A61G 19/00 | (2006.01) |
| A61G 12/00 | (2006.01) |
| B62B 3/00 | (2006.01) |
| F16M 11/42 | (2006.01) |
| F16M 13/02 | (2006.01) |
| A61G 5/10 | (2006.01) |
| F16M 11/04 | (2006.01) |
| A61M 16/16 | (2006.01) |
| G06F 1/16 | (2006.01) |

(52) U.S. Cl.
CPC .......... *A61M 16/0003* (2014.02); *A61G 5/10* (2013.01); *A61G 5/1094* (2016.11); *F16M 11/041* (2013.01); *F16M 11/42* (2013.01); *F16M 13/02* (2013.01); *F16M 13/022* (2013.01); *A61M 16/16* (2013.01); *A61M 2209/082* (2013.01); *B62B 3/00* (2013.01); *G06F 1/16* (2013.01)

(58) Field of Classification Search
CPC ........ A61M 16/0003; A61M 2209/082; A61M 16/16; F16M 13/022; F16M 11/42; F16M 11/041; F16M 13/02; A61G 5/10; A61G 5/1094; G06F 1/16; B62B 3/00
See application file for complete search history.

(56) References Cited

U.S. PATENT DOCUMENTS 6,459,027 B1 * 10/2002 Van Dermeulen ... G10D 13/026
84/327
7,294,775 B1 * 11/2007 Spoljaric, Jr. ........ G10D 13/026
224/268

(Continued)

FOREIGN PATENT DOCUMENTS

EP 2214617 B1 6/2015
WO 2015074360 A1 5/2015

*Primary Examiner* — Tan Le
(74) *Attorney, Agent, or Firm* — Daniel H. Brean

(57) ABSTRACT

The present disclosure pertains to a ventilator mount system. The system includes a ventilator mount configured to mount a ventilator thereon; a platform configured to be carried by a stand; and a releasable lock assembly configured to affix the ventilator mount to the platform. In some embodiments, the lock assembly is configured to be moved between a locked position and a release position. In some embodiments, the ventilator mount is releasable from the platform when the lock assembly is moved from the locked position to the release position.

20 Claims, 6 Drawing Sheets

(56) References Cited

U.S. PATENT DOCUMENTS

| | | | |
|---|---|---|---|
| 8,233,272 B2* | 7/2012 | Fidacaro | A61B 5/0002 340/870.01 |
| 8,821,367 B2* | 9/2014 | Khodak | A61G 11/00 600/22 |
| 9,560,976 B2* | 2/2017 | Lane | A61B 5/02055 |
| 2002/0044059 A1 | 4/2002 | Reeder | |
| 2005/0017147 A1 | 1/2005 | Fuelling | |
| 2010/0148458 A1 | 6/2010 | Ross | |
| 2011/0054268 A1 | 3/2011 | Fidacaro et al. | |
| 2011/0227237 A1 | 9/2011 | Hertz | |
| 2016/0363262 A1 | 12/2016 | Moelmann | |

* cited by examiner

VENTILATOR MOUNT SYSTEM

CROSS-REFERENCE TO RELATED APPLICATIONS

This patent application claims the priority benefit under 35 U.S.C. § 119(e) of U.S. Provisional Application No. 62/527,071, filed on Jun. 30, 2017, the contents of which are herein incorporated by reference.

BACKGROUND OF THE INVENTION

1. Field of the Invention

The present disclosure pertains to a ventilator mount system.

2. Description of the Related Art

It is well known that ventilators are frequently mounted onto roll stands to help with therapy mobility within a hospital or home. Ventilators may include different mounting solutions, each mounting solution being specifically designed for a particular roll stand. Current mounting solutions may not provide adequate stability or may render mounting of the ventilator on the roll stand difficult. These and other drawbacks exist.

SUMMARY OF THE INVENTION

Accordingly, one or more aspects of the present disclosure relate to a ventilator mount system. The system comprises a ventilator mount configured to mount a ventilator thereon. The system comprises a platform configured to be carried by a stand. The system comprises a releasable lock assembly configured to affix the ventilator mount to the platform. The lock assembly is configured to be moved between a locked position and a release position. The ventilator mount is releasable from the platform when the lock assembly is moved from the locked position to the release position.

Yet another aspect of the present disclosure relates to a method for facilitating mounting a ventilator on a stand. The method comprises providing a ventilator mount configured to mount a ventilator thereon. The method comprises providing a platform configured to be carried by a stand. The method comprises affixing the ventilator mount to the platform with a releasable lock assembly. The lock assembly is configured to be moved between a locked position and a release position. The ventilator mount is releasable from the platform when the lock assembly is moved from the locked position to the release position.

Still another aspect of present disclosure relates to a system for facilitating mounting a ventilator on a stand. The system comprises ventilator mount means configured to mount a ventilator thereon. The system comprises platform means configured to be carried by a stand. The system comprises releasable lock means configured to affix the ventilator mount to the platform. The lock means is configured to be moved between a locked position and a release position. The ventilator mount means is releasable from the platform means when the lock means is moved from the locked position to the release position.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
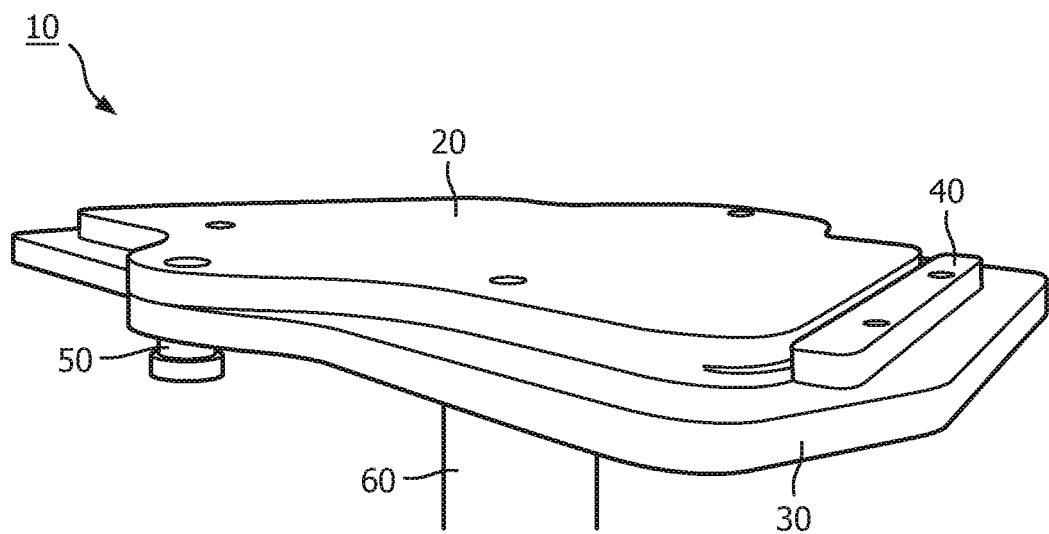
FIG. 1 illustrates a perspective view of a ventilator mount system, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Current mounting solutions may include a pair a parallel flanges disposed on a plate in which a ventilator mount is slid there between. Such mounting systems may not provide sufficient visibility to a user during the mounting process. As such, these systems may require precise two-handed alignment of the ventilator mount with the flanges. Other mounting solutions include placing the ventilator directly on top of one or more pins protruding from a platform. These mounting systems may be prone to detachment of the ventilator in a vertical direction.

FIG. 1 illustrates a perspective view of ventilator mount system 10, in accordance with one or more embodiments. Ventilator mount system 10 comprises a ventilator mount 20, a platform 30, a lock assembly including a pair of flanges 40 and spring-loaded plunger 50, and/or other components. Ventilator mount system 10 facilitates convenient mounting of a ventilator on a stand 60 by (i) slidably engaging ventilator mount 20 with flanges 40 and (ii) releasably securing mount 20 to platform 30 via spring-loaded plunger 50.

Figure 2:
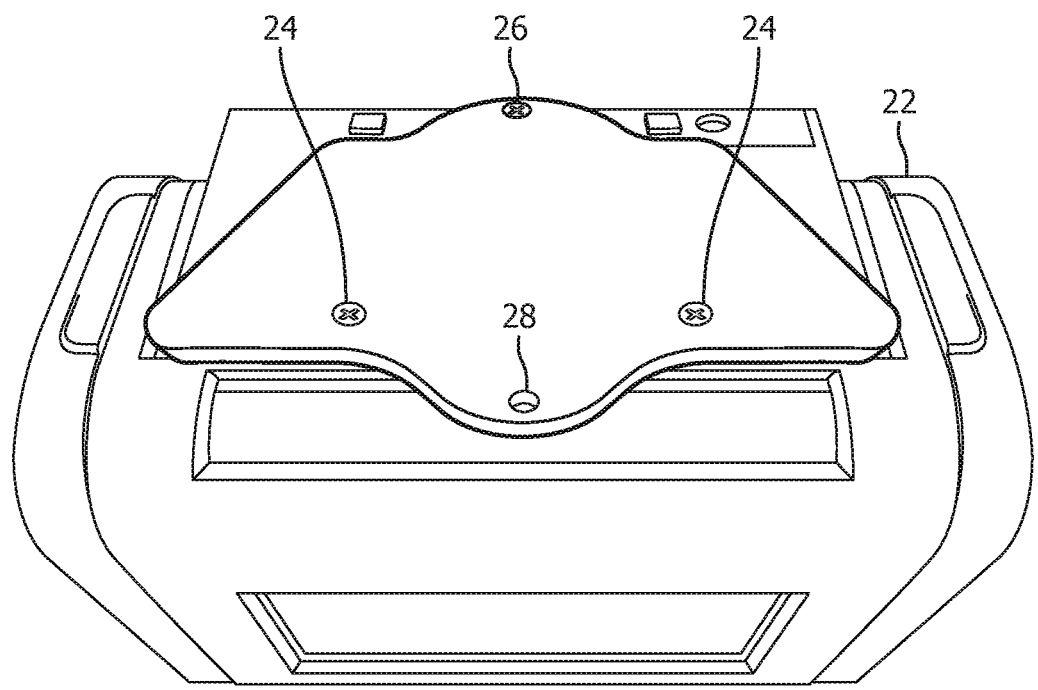
FIG. 2 illustrates a ventilator being releasably coupled to a ventilator mount via one or more screws, in accordance with one or more embodiments.

In some embodiments, ventilator mount 20 is configured to mount a ventilator 22 thereon. In some embodiments, ventilator mount 20 comprises one or more screw cavities 24. In some embodiments, ventilator mount 20 is configured to be releasably coupled to the ventilator 22 via one or more screws 26 releasably protruding from ventilator mount screw cavities 24. By way of a non-limiting example, FIG. 2 illustrates ventilator 22 being releasably coupled to ventilator mount 20 via one or more screws 26, in accordance with one or more embodiments. In some embodiments, ventilator mount 20 comprises a thermoplastic (e.g., Polyoxymethylene) and/or other materials. In some embodiments, the thermoplastic includes Delrin, and/or other polymers and materials.

Figure 3:
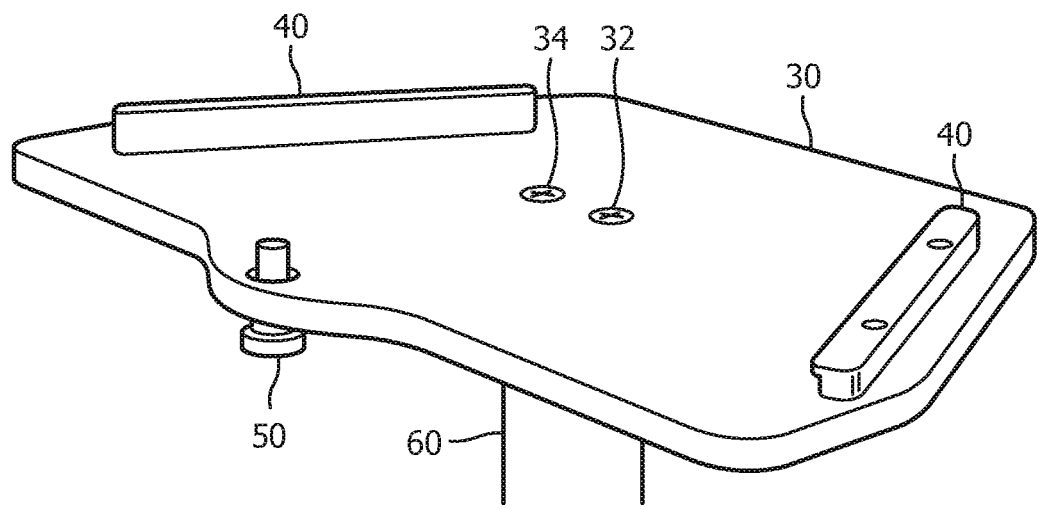
FIG. 3 illustrates a platform being carried by a stand, in accordance with one or more embodiments.

Returning to FIG. 1, platform 30 is configured to be carried by stand 60. In some embodiments, platform 30 comprises one or more screw cavities 32. In some embodiments, platform 30 is configured to be releasably coupled with stand 60 via one or more screws 34 configured to releasably protrude from one or more platform screw cavities 32. In some embodiments, one or more screw cavities 32 are disposed at a center of mass of platform 30. By way of a non-limiting example, FIG. 3 illustrates platform 30 being carried by stand 60, in accordance with one or more embodiments. In some embodiments, stand 60 comprises a roll stand and/or other stands. In some embodiments, platform 30 comprises aluminum and/or other materials.

Figure 4:
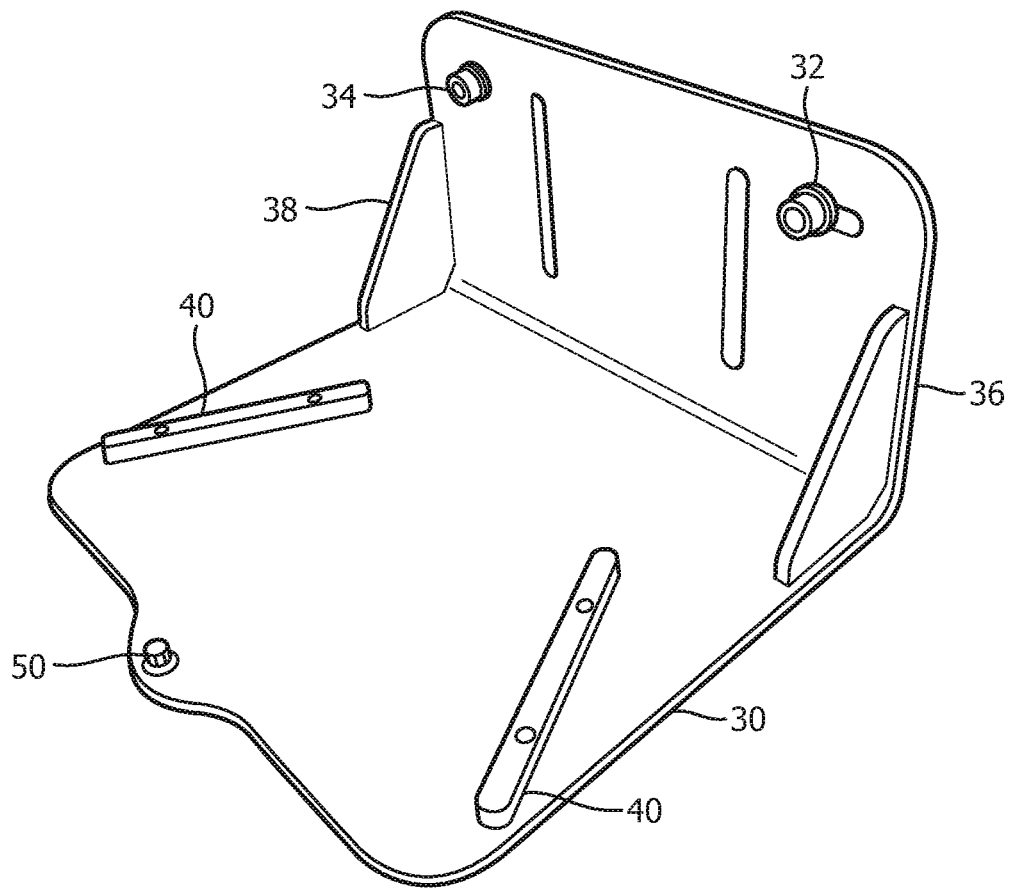
FIG. 4 illustrates a platform configured to be coupled with a wheelchair, in accordance with one or more embodiments.
Figure 5:
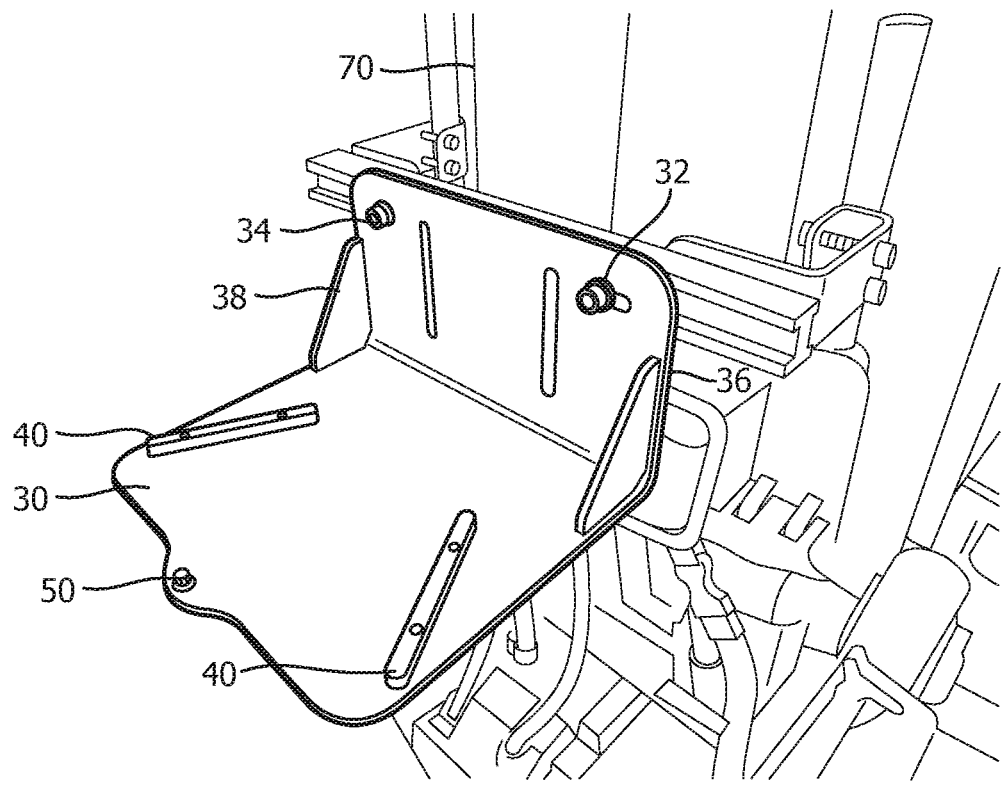
FIG. 5 illustrates a platform coupled with a wheelchair, in accordance with one or more embodiments.

In some embodiments, stand 60 comprises a wheelchair. In some embodiments, platform 30 comprises a stop surface 36 configured to engage a portion of a wheelchair. By way of a non-limiting example, FIG. 4 illustrates platform 30 configured to be coupled with a wheelchair, in accordance with one or more embodiments. In some embodiments, stop surface 36 is substantially perpendicular to platform 30. In some embodiments, one or more screw cavities 32 are disposed on stop surface such that platform 30 is releasably coupled with a wheelchair via one or more screws 34 configured to releasably protrude from one or more screw cavities 32. By way of a non-limiting example, FIG. 5 illustrates platform 30 coupled with wheelchair 70, in accordance with one or more embodiments. In some embodiments, platform 30 comprises one or more brackets 38 disposed between platform 30 and stop surface 36. One or more brackets 38 are configured to secure stop surface 36 to platform 30. In some embodiments, one or more brackets 38 are configured to maintain an angle between stop surface 36 and platform 30 a constant in response to a ventilator being mounted on platform 30.

Returning to FIG. 1, system 10 comprises a releasable lock assembly configured to affix ventilator mount 20 to platform 30. In some embodiments, the lock assembly comprises a manual actuator that is manually moved from the locked position to the release position to release the lock.

In some embodiments, the actuator comprises a manually engageable and movable structure that facilitates the lock assembly to be released. In some embodiments, the manual actuator comprises spring-loaded plunger 50. In some embodiments, platform 30 has a first surface (e.g., top surface) and a second surface (e.g., bottom surface) opposite the first surface. In some embodiments, plunger 50 is disposed on the second surface. In some embodiments, plunger 50 is configured to be moved between a locked position and a release position. In some embodiments, ventilator mount 20 is releasable from platform 30 when the plunger 50 is moved from the locked position to the release position. In some embodiments, ventilator mount 20 comprises a first end and a second end opposite the first end. In some embodiments, ventilator mount 20 comprises at least one cavity 28 disposed at the first end (see, e.g., FIG. 2). In some embodiments, responsive to ventilator mount 20 engaging with flanges 40 (described below), spring-loaded plunger 50 is configured to releasably couple with the at least one cavity 28 to secure ventilator mount 20 to platform 30. In some embodiments, responsive to a force substantially perpendicular to platform 30 being applied to plunger 50, plunger 50 is configured to be moved from the locked position to the release position. Referring to FIG. 3, plunger 50 in a relaxed state (e.g., closed position) protrudes from platform 30 to prevent ventilator mount 20 from sliding further in or out while engaged with platform 30. In this example, responsive to plunger 50 being in an extended state (e.g., open position) via a pulling force, ventilator mount 20 may be disengaged from platform 30. In some embodiments, plunger 50 is constructed from stainless steel and/or other materials.

Returning to FIG. 1, the releasable lock assembly comprises a pair of flanges 40 disposed on the first surface of platform 30. In some embodiments, flanges 40 are spaced apart from one another such that a slidable engagement between ventilator mount 20 and flanges 40 is facilitated. In some embodiments, flanges 40 are disposed at a first side (e.g., right side) and a second side (e.g., left side) opposite the first side of platform 30. In some embodiments, flanges 40 are disposed at an angle with respect to one another (e.g., not parallel) to prevent ventilator mount 20 from sliding further in while engaged with platform 30. In some embodiments, individual ones of the pair of flanges 40 are constructed from a solid piece of metal. In some embodiments, individual ones of the pair of flanges 40 are constructed from a plurality of metal pieces continuously and/or intermittently spaced from each other. In some embodiments, flanges 40 are constructed from aluminum and/or other metals.

Figure 6:
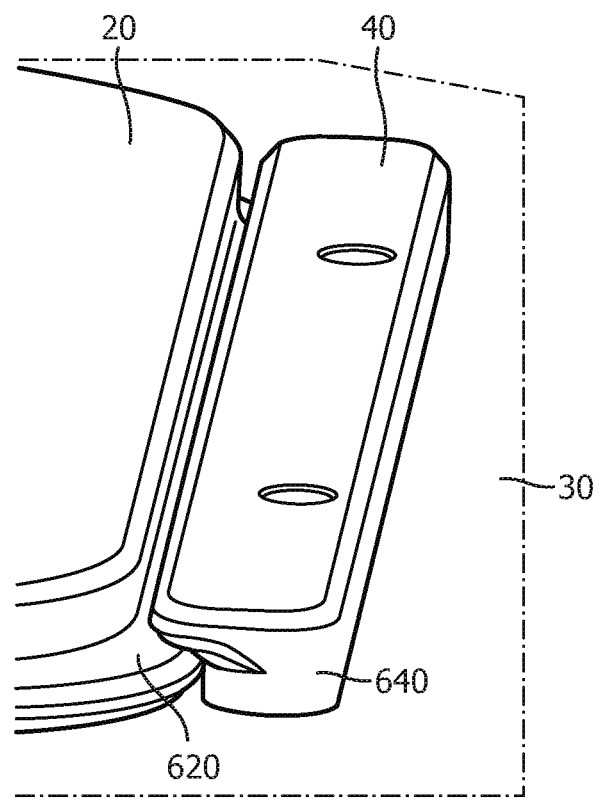
FIG. 6 illustrates a recessed portion of a ventilator mount being engaged with a flange undercut, in accordance with one or more embodiments.

In some embodiments, ventilator mount 20 comprises a first side (e.g., right side) and a second side (e.g., left side) opposite the first side. In some embodiments, a surface of ventilator mount 20 comprises recessed portions on the first side and the second side. In some embodiments, individual ones of the pair of flanges 40 comprise an undercut (e.g., a recessed portion) facing a center of platform 30. In some embodiments, the ventilator mount recessed portions engage with the flanges' undercuts such that ventilator mount 20 is secured to platform 30. By way of a non-limiting example, FIG. 6 illustrates a recessed portion of ventilator mount 20 being engaged with flange 40 undercut, in accordance with one or more embodiments. As shown in FIG. 6, ventilator mount 20 is configured to slidably engage with flanges 40 via the recessed portions 620 of ventilator mount 20 being received in undercut portions 640 of flanges 40.

Figure 7:
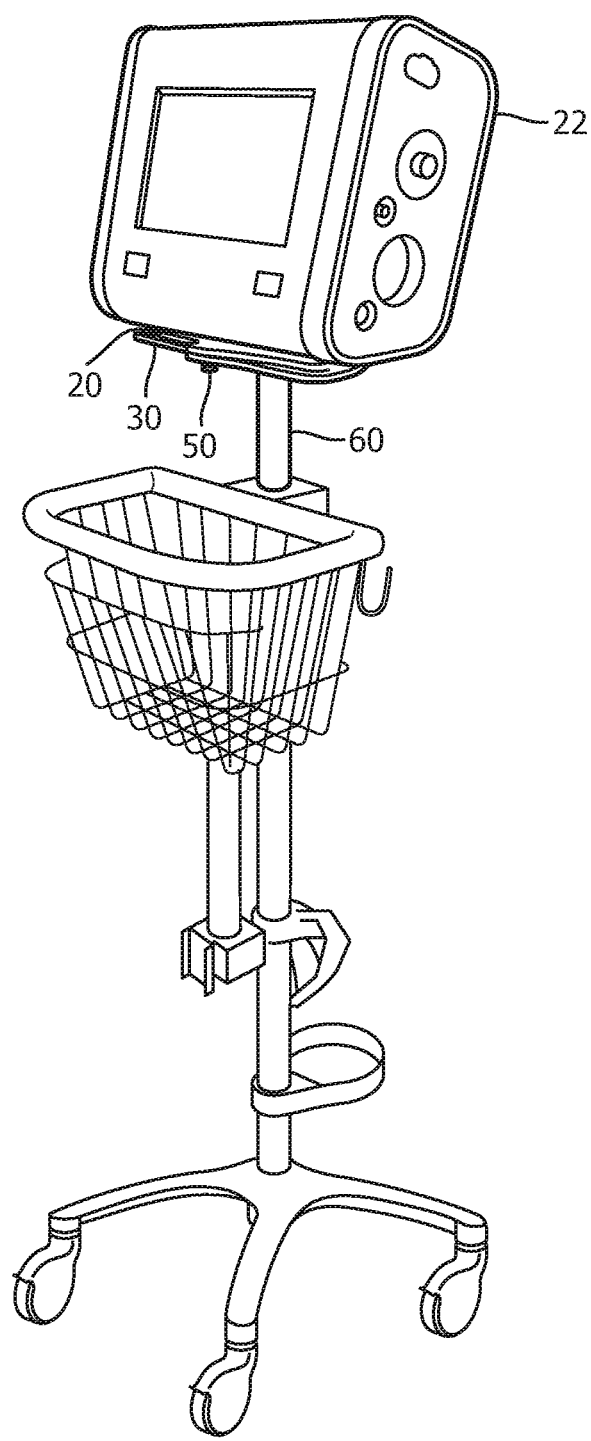
FIG. 7 illustrates a ventilator being mounted on a roll-stand, in accordance with one or more embodiments.

FIG. 7 illustrates a ventilator 22 being mounted on a roll-stand, in accordance with one or more embodiments. As shown in FIG. 7, ventilator 22 is mounted on top of ventilator mount 20, platform 30 is mounted on a pole of a roll stand, and ventilator mount 20 is affixed to platform 30.

Figure 8:
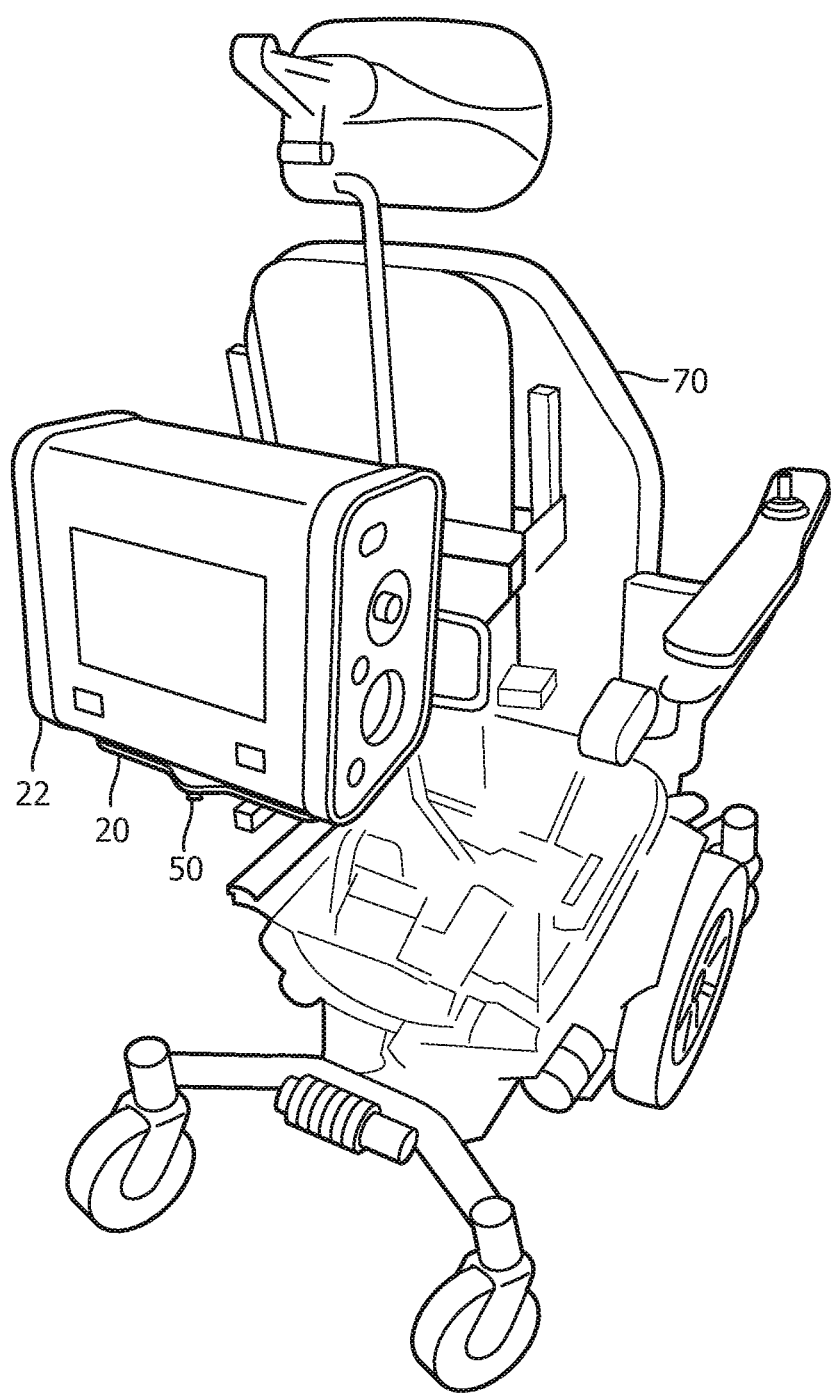
FIG. 8 illustrates a ventilator being mounted on a wheelchair, in accordance with one or more embodiments.

FIG. 8 illustrates a ventilator 22 being mounted on a wheelchair, in accordance with one or more embodiments. As shown in FIG. 8, ventilator 22 is mounted on top of ventilator mount 20, stop surface 36 is mounted on a backside of a wheelchair, and ventilator mount 20 is affixed to platform 30.

Figure 9:
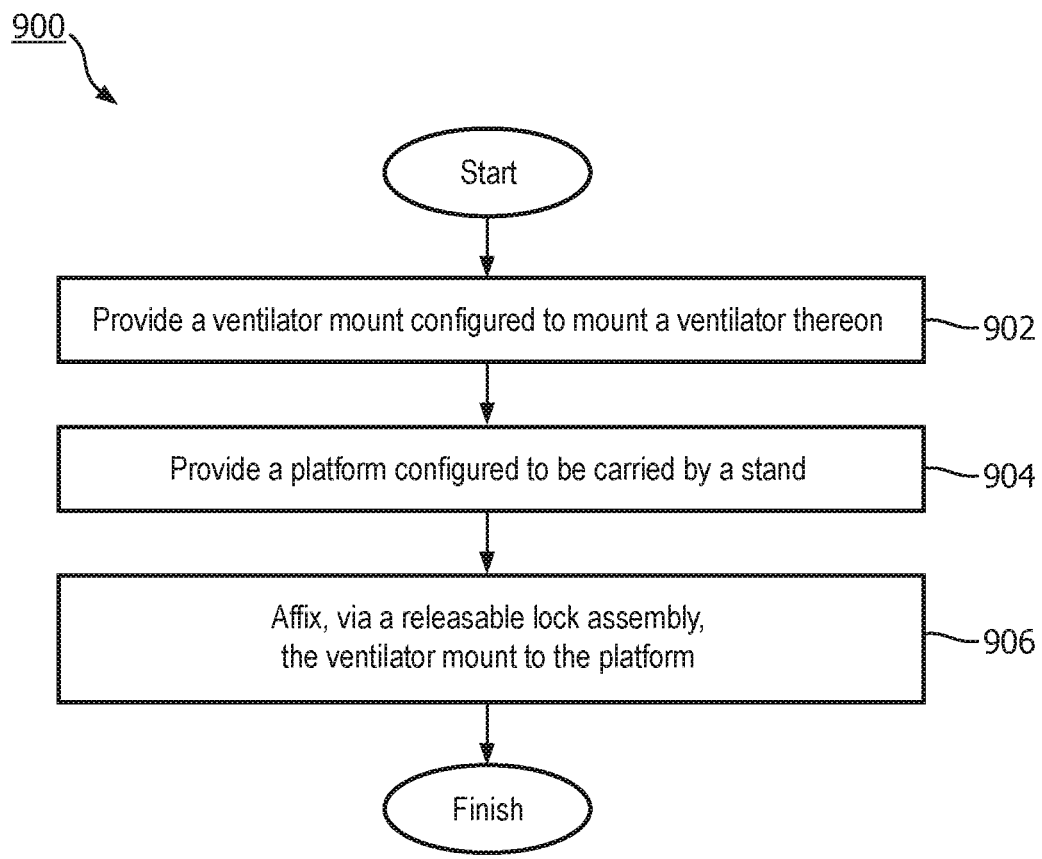
FIG. 9 illustrates method for facilitating mounting a ventilator on a stand, in accordance with one or more embodiments.

FIG. 9 illustrates method 900 for facilitating mounting a ventilator on a stand, in accordance with one or more embodiments. The operation of method 900 presented below is intended to be illustrative. In certain embodiments, method 900 may be accomplished with one or more additional operations not described, and/or without one or more of the operations discussed. Additionally, the order in which the operations of method 900 are illustrated in FIG. 9 and described below is not intended to be limiting.

At an operation 902, a ventilator mount configured to mount a ventilator thereon is provided. In some embodiments, operation 902 is performed by a ventilator mount the same as or similar to ventilator mount 20 (shown in FIG. 1 and described herein).

At an operation 904, a platform configured to be carried by a stand is provided. In some embodiments, operation 904 is performed by a platform the same as or similar to platform 30 (shown in FIG. 1 and described herein).

At an operation 906, the ventilator mount is affixed to the platform with a releasable lock assembly. In some embodiments, the lock assembly is configured to be moved between a locked position and a release position. In some embodiments, the ventilator mount is releasable from the platform when the lock assembly is moved from the locked position to the release position. In some embodiments, operation 906 is performed by a lock assembly the same as or similar to flanges 40 and plunger 50 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claims is:

1. A ventilator mount system, comprising:
a ventilator mount configured to be coupled to a ventilator, the ventilator mount having a first surface positioned to contact the ventilator when the ventilator is coupled to the ventilator mount and a second surface opposite the first surface;
a platform configured to be carried by a stand, the platform having a first surface and a second surface opposite the first surface;
a releasable lock assembly configured to affix the ventilator mount to the platform such that the second surface of the ventilator mount is disposed against the first surface of the platform, the lock assembly configured to be moved between a locked position, in which at least a portion of the lock assembly extends outward from the first surface of the platform, and a release position, in which the portion of the lock assembly does not extend outward from the first surface of the platform, wherein the ventilator mount is releasable from the platform when the lock assembly is moved from the locked position to the release position; and
a pair of flanges extending outward from the first surface of the platform at an angle with respect to one another.

2. The ventilator mount system of claim 1, wherein the stand comprises a roll stand or wheelchair.

3. The ventilator mount system of claim 1, wherein the lock assembly comprises a spring-loaded plunger.

4. The ventilator mount system of claim 3, wherein responsive to a force substantially perpendicular to the platform being applied to the plunger, the plunger is configured to be moved from the locked position to the release position.

5. The system of claim 3, wherein the ventilator mount comprises a first side extending between the first surface and the second surface of the ventilator mount and a second side extending between the first surface and the second surface of the ventilator mount opposite the first side, wherein the first side and the second side comprise recessed portions, and wherein the recessed portions engage with the flanges such that the ventilator mount is secured to the platform.

6. The system of claim 5, wherein ventilator mount comprises a first end and a second end opposite the first end, wherein the ventilator mount comprises at least one cavity disposed at the first end, and wherein responsive to the ventilator mount engaging with the flanges, the spring-loaded plunger is configured to releasably couple with the at least one cavity to secure the ventilator mount to the platform.

7. The ventilator mount system of claim 1, wherein the platform comprises one or more screw cavities, wherein the platform is configured to be releasably coupled with the stand via one or more screws configured to releasably protrude from the one or more platform screw cavities, and wherein the ventilator mount comprises one or more screw cavities, and wherein the ventilator mount is configured to be releasably coupled to the ventilator via one or more screws releasably protruding from the ventilator mount screw cavities.

8. The ventilator mount system of claim 1, wherein the ventilator mount comprises a thermoplastic and wherein the platform comprises aluminum.

9. The ventilator mount system of claim 1, wherein the lock assembly comprises a manual actuator that is manually moved from the locked position to the release position to release the lock.

10. A method for facilitating mounting a ventilator on a stand, the method comprising:
providing a ventilator mount configured to be coupled to a ventilator, the ventilator mount having a first surface positioned to contact the ventilator when the ventilator is coupled to the ventilator mount and a second surface opposite the first surface;

providing a platform configured to be carried by a stand, the platform having a first surface and a second surface opposite the first surface; and affixing, via a releasable lock assembly and a pair of flanges extending outward from the first surface of the platform at an angle with respect to one another, the ventilator mount to the platform, the lock assembly configured to be moved between a locked position and a release position, the ventilator mount being releasable from the platform when the lock assembly is moved from the locked position to the release position.

11. The method of claim 10, wherein the stand comprises a roll stand or wheelchair.

12. The method of claim 10, wherein the lock assembly comprises a spring-loaded plunger.

13. The method of claim 12, wherein responsive to a force substantially perpendicular to the platform being applied to the plunger, the plunger is configured to be moved from the locked position to the release position.

14. The method of claim 13, wherein the ventilator mount comprises a first side extending between the first surface and the second surface of the ventilator mount and a second side extending between the first surface and the second surface of the ventilator mount opposite the first side, wherein the first side and the second side comprise recessed portions, and wherein the recessed portions engage with the flanges such that the ventilator mount is secured to the platform.

15. The method of claim 14, wherein ventilator mount comprises a first end and a second end opposite the first end, wherein the ventilator mount comprises at least one cavity disposed at the first end, and wherein responsive to the ventilator mount engaging with the flanges, the spring-loaded plunger is configured to releasably couple with the at least one cavity to secure the ventilator mount to the platform.

16. The method of claim 10, wherein the platform comprises one or more screw cavities, wherein the platform is configured to be releasably coupled with the stand via one or more screws configured to releasably protrude from the one or more platform screw cavities, wherein the ventilator mount comprises one or more screw cavities, and wherein the ventilator mount is configured to be releasably coupled to the ventilator via one or more screws releasably protruding from the ventilator mount screw cavities.

17. The method of claim 10, wherein the ventilator mount comprises a thermoplastic and wherein the platform comprises aluminum.

18. The method of claim 10, wherein the lock assembly comprises a manual actuator that is manually moved from the locked position to the release position to release the lock.

19. The method of claim 10, wherein the first surface of the platform and the second surface of the ventilator mount are planar surfaces.

20. The ventilator mount system of claim 1, wherein the first surface of the platform and the second surface of the ventilator mount are planar surfaces.

* * * * *